(12) United States Patent
Grajcar

(10) Patent No.: US 9,185,888 B2
(45) Date of Patent: Nov. 17, 2015

(54) AQUACULTURE LIGHTING DEVICES AND METHODS

(71) Applicant: Once Innovations, Inc., Plymouth, MN (US)

(72) Inventor: Zdenko Grajcar, Orono, MN (US)

(73) Assignee: Once Innovations, Inc., Plymouth, MN (US)

( * ) Notice: Subject to any disclaimer, the term of this patent is extended or adjusted under 35 U.S.C. 154(b) by 0 days.

(21) Appl. No.: 14/463,861

(22) Filed: Aug. 20, 2014

(65) Prior Publication Data

US 2014/0355254 A1  Dec. 4, 2014

Related U.S. Application Data

(63) Continuation-in-part of application No. 13/715,904, filed on Dec. 14, 2012.

(60) Provisional application No. 61/868,352, filed on Aug. 21, 2013.

(51) Int. Cl.
| | |
|---|---|
| *A01K 61/00* | (2006.01) |
| *A01K 63/06* | (2006.01) |
| *F21V 29/58* | (2015.01) |
| *A01G 33/00* | (2006.01) |

(Continued)

(52) U.S. Cl.
CPC ............ *A01K 63/06* (2013.01); *A01G 33/00* (2013.01); *A01K 61/00* (2013.01); *A01K 61/005* (2013.01); *C12M 21/02* (2013.01); *C12M 31/10* (2013.01); *C12N 1/12* (2013.01); *C12N 13/00* (2013.01); *F21V 3/0418* (2013.01);

(Continued)

(58) Field of Classification Search
CPC ...... A01K 61/00; A01K 61/005; A01K 63/06; F21V 31/00
USPC ......... 119/204, 245, 266, 267, 269, 233, 215; 362/294
See application file for complete search history.

(56) References Cited

U.S. PATENT DOCUMENTS

| | | | | |
|---|---|---|---|---|
| 2,709,984 | A | * | 6/1955 | Marks ........................... 119/220 |
| 3,939,802 | A | * | 2/1976 | Neff ........................... 119/51.04 |

(Continued)

FOREIGN PATENT DOCUMENTS

| | | |
|---|---|---|
| CN | 1042039 A | 5/1990 |
| CN | 1692700 A | 11/2005 |

(Continued)

OTHER PUBLICATIONS

Hongshan Su: "Fish Culture in Light Net Pen Underwater" (title also translated as "Test of Fish Farming in Underwater Lighting Cage"), Journal of Zoology, vol. 2,1983, pp. 31-32, with English translation.

(Continued)

*Primary Examiner* — Yvonne Abbott-Lewis

(57) ABSTRACT

A lighting assembly for enhancing the growth of aquatic life in an ecosystem and method of enhancing the growth of aquatic life in such an ecosystem. The assembly includes a vessel submerged within water of the ecosystem. A substrate is disposed within and surrounded by the vessel and provides electronics to provide a conditioned current to a plurality of light emitting diodes also contained on the substrate. The light emitting diodes emit light within the water of the ecosystem that provides for growth, not only in a larger volume of the ecosystem, but in addition enhances the growth of the aquatic life.

7 Claims, 12 Drawing Sheets

(51) Int. Cl.

| | | |
|---|---|---|
| *C12M 1/00* | (2006.01) | |
| *C12N 1/12* | (2006.01) | |
| *C12N 13/00* | (2006.01) | |
| *F21V 3/04* | (2006.01) | |
| *F21V 31/00* | (2006.01) | |
| *H01L 33/58* | (2010.01) | |
| *H01L 33/64* | (2010.01) | |
| *F21S 2/00* | (2006.01) | |
| *F21V 23/04* | (2006.01) | |
| *F21Y 101/02* | (2006.01) | |
| *F21Y 103/00* | (2006.01) | |
| *F21V 21/08* | (2006.01) | |
| *H01L 23/00* | (2006.01) | |

(52) U.S. Cl.
CPC ............. *F21V 3/0472* (2013.01); *F21V 29/58* (2015.01); *F21V 31/00* (2013.01); *H01L 33/58* (2013.01); *H01L 33/64* (2013.01); *F21S 2/00* (2013.01); *F21V 21/0824* (2013.01); *F21V 23/04* (2013.01); *F21V 23/0442* (2013.01); *F21Y 2101/02* (2013.01); *F21Y 2103/003* (2013.01); *H01L 24/48* (2013.01); *H01L 33/648* (2013.01); *H01L 2224/48091* (2013.01); *H01L 2924/13091* (2013.01); *Y10T 29/4973* (2015.01)

(56) References Cited

U.S. PATENT DOCUMENTS

| | | | | |
|---|---|---|---|---|
| 4,137,869 | A * | 2/1979 | Kipping | 119/230 |
| 4,379,437 | A * | 4/1983 | Knowles | 119/230 |
| 4,699,086 | A * | 10/1987 | Mori | 119/51.04 |
| 4,699,087 | A * | 10/1987 | Mori | 119/51.04 |
| 4,703,719 | A * | 11/1987 | Mori | 119/51.04 |
| 5,027,550 | A | 7/1991 | Mori | |
| 5,161,481 | A * | 11/1992 | Laufer | 119/205 |
| 5,713,303 | A * | 2/1998 | Willinsky et al. | 119/218 |
| 5,850,806 | A * | 12/1998 | Mark et al. | 119/219 |
| 5,937,791 | A * | 8/1999 | Baugher et al. | 119/219 |
| 6,347,908 | B1 * | 2/2002 | Safwat | 405/81 |
| 7,220,018 | B2 * | 5/2007 | Crabb et al. | 362/234 |
| 8,100,560 | B2 * | 1/2012 | Ahland et al. | 362/267 |
| 2002/0191396 | A1 * | 12/2002 | Reiff et al. | 362/246 |
| 2007/0159833 | A1 * | 7/2007 | Netzel et al. | 362/373 |
| 2007/0268702 | A1 * | 11/2007 | McFadden | 362/294 |
| 2010/0268390 | A1 * | 10/2010 | Anderson | 700/284 |
| 2011/0253056 | A1 * | 10/2011 | Fredricks | 119/247 |
| 2012/0060763 | A1 * | 3/2012 | Lin | 119/267 |
| 2013/0333627 | A1 * | 12/2013 | Pohl | 119/263 |

FOREIGN PATENT DOCUMENTS

| | | |
|---|---|---|
| CN | 201344401 Y | 11/2009 |
| CN | 101868529 A | 10/2010 |
| WO | 2009-066231 A2 | 5/2009 |

OTHER PUBLICATIONS

Office Action issued in Chinese Application No. 201280070124.6, dated May 18, 2015, with English translation.

* cited by examiner

AQUACULTURE LIGHTING DEVICES AND METHODS

CROSS REFERENCE

This application claims the benefit of U.S. Provisional Patent Application entitled "Aquaculture Lighting Devices and Methods" Ser. No. 61/868,352, which was filed by Z. Grajcar on Aug. 21, 2013 the entire contents of each of which are incorporated herein by reference. This application also claims benefit to and is a continuation in part of U.S. Ser. No. 13/715,904 entitled Aquaculture Lighting Devices and Methods filed on Dec. 13, 2012 that is based upon and claims priority to U.S. Provisional Patent Application Ser. No. 61/570,552 filed Dec. 14, 2011 entitled LED Lighting Structures and that application is incorporated by reference in full.

BACKGROUND

This invention is related to LED Lighting Assemblies. More specifically, this invention relates to an underwater LED lighting assembly for enhancing aquaculture in natural and man-made ecosystems.

Lighting can be used to affect the growth of aquatic animals. Specifically, light is needed for growth of most animal species and substantially affects the animals' behavior in terms of feeding, reproducing, location in the water column, and other factors. Water naturally filters light as the water gets deeper, such that lower light intensity and a different spectrum of light wavelengths reaches deep water.

In aquaculture, carbon dioxide ($CO_2$) and oxides of nitrogen contaminate the water and create an environment that is lethal to certain animals. In nature, algae in the water can consume both $CO_2$ and nitrogen in the course of algae growth and photosynthesis; in so doing, the algae decontaminates the water while providing food to the animals. In order to use algae for such purposes, however, light needs to be present at proper frequencies and intensities to allow the algae to grow using photosynthesis. The quantity of light available in a water pond may be reduced by: 1) less than ideal periods of sunlight being present during a 24 hour solar cycle to permit photosynthesis to take place as may be desired; 2) the reflective nature of the water surface, which reflectance reduces the beneficial effect of available light on photosynthesis, and which reflectance changes as the angle of the sun to the water moves from acute to oblique as the day progresses, thus inhibiting photosynthesis, and 3) the fact that water containing high levels of solids (whether in the form of decaying or living matter, such as decaying or living algae) does not permit light to reach much beyond the surface. When the light in a water pond is reduced, photosynthesis can be reduced or become impossible, and the benefits of photosynthesis may be absent at any depth much below the surface. As such, the use of deeper water levels in aquaculture facilities may prove to be problematic.

Small ponds have several factors which inhibit light penetration into the pond, including lack of wave action, as the smaller body of water is more protected and picks up less wind energy. Without wave action, more light is reflected off of the surface of the water and does not penetrate into the pond (in contrast, with constant wave action, the sun's rays are only reflected a portion of the time and less of the sunlight is reflected as the continuously changing surface does not create a smooth reflective surface). Some measurements estimate that on a smooth surface pond, only 40% of the light energy penetrates the surface of the water. After a certain point, beyond the critical angle, all of the light is reflected off the surface and it becomes dark underwater (although it is still light above the water).

Protection also reduces the clearing of the water surface, and algae or other materials may come to rest on the surface and cloud the surface, which otherwise might have been blown from the surface of the pond and/or dissipated into a larger body of water. The animals may need to have different spectra of light passed to them for different depths of water. For example, a fish whose habitat is within a one meter depth from the surface of a pond may thrive with a different light spectrum than a fish whose habitat is deeper within the pond (e.g., at a depth of 10 meters).

Further, studies have shown that different living organisms are both physiologically and psychologically affected by the wavelength of light they receive. This holds true whether the living organism is a plant or animal as is discussed in several patents by the present inventor, including provisional patent application 61/669,825 entitled Light Sources Adapted to Spectral Sensitivity of Plants to Grajcar and 61/698,074 entitled Aquatic System for Manipulating Psychological and Physiological Effects in Aquatic Life to Grajcar, both that are incorporated in full herein.

Thus, a need in the art exists for an underwater lighting assembly that can be used to enhance and grow aquatic life in its natural habitat and also in man-made facilities. Further a need in the art exists to increase the yield, size and capacity for aquatic life.

Therefore, a principle object of the present invention is to provide a submergible LED lighting assembly for aquatic life;

Yet another object of the present invention is to optimize the growth and yield of aquatic life.

Another object of the present invention is to provide additional locations in which aquatic life can be grown for harvesting.

These and other objects, features and advantages will become apparent from the specification and claims.

SUMMARY OF THE INVENTION

A lighting assembly for enhancing the growth of aquatic life in an ecosystem and method of enhancing the growth of aquatic life in such an ecosystem. The assembly includes a vessel submerged within water of the ecosystem that contains a substrate disposed therein. The substrate has driving circuitry thereon to supply current to a plurality of light emitting diodes electrically connected to the driving circuitry. The light emitting diodes emit light within the water of the ecosystem that provides for growth, not only in a larger volume of the ecosystem, but in addition enhances the growth of the aquatic life.

The assembly can also include a control system, anchoring system and cleaning system for enhancing the performance of the assembly. In addition, the assembly provides both light duration and color or spectra control to allow a user to optimize the lighting output based on predetermined attributes of the aquatic life and ecosystem to optimize yield and growth of the aquatic life.

DETAILED DESCRIPTION OF A PREFERRED EMBODIMENT OF THE INVENTION

Figure 1:
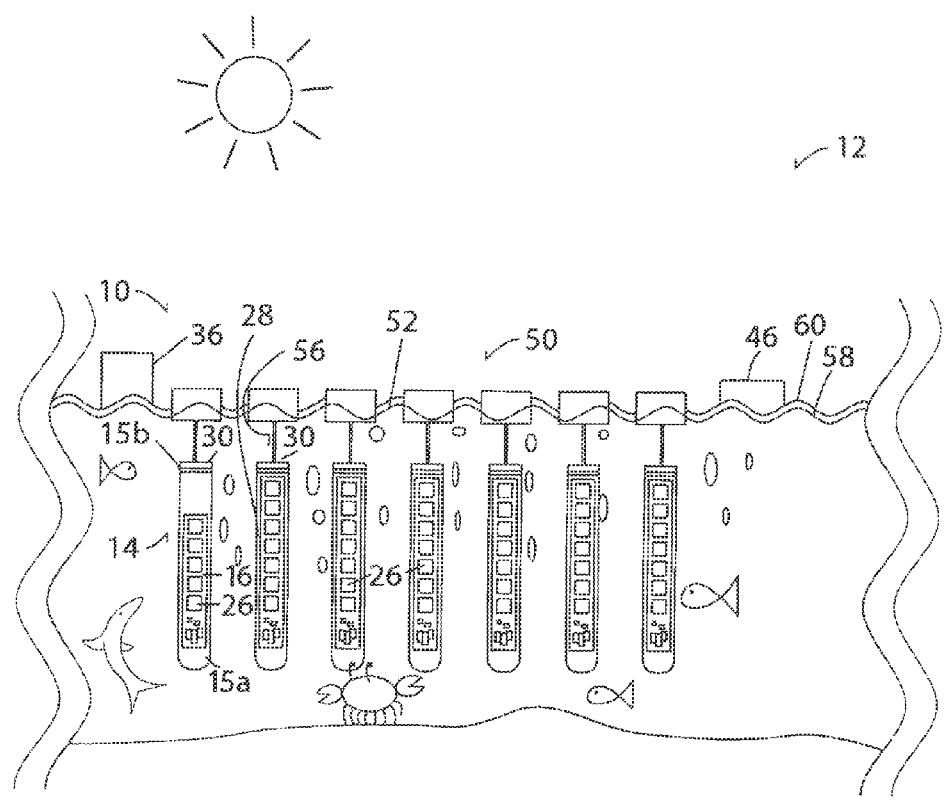
FIG. 1 is a side plan view of a lighting assembly within an ecosystem.
Figure 2:
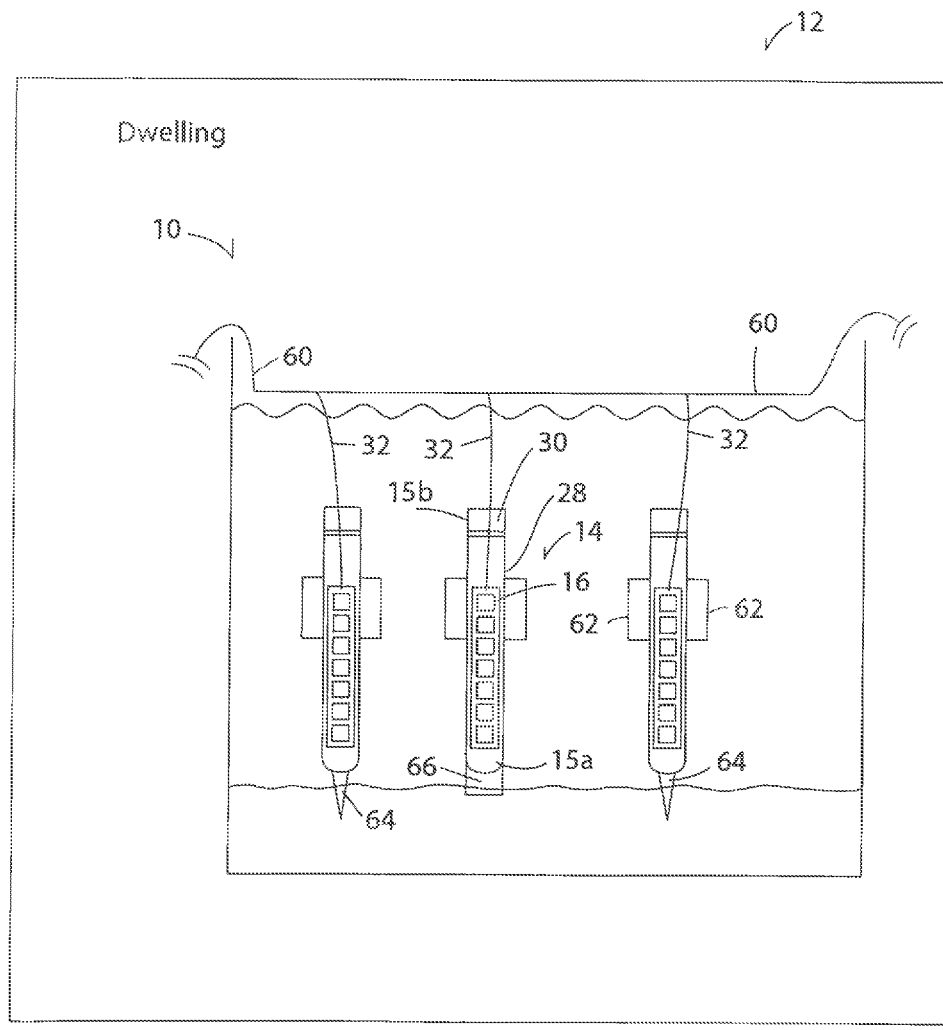
FIG. 2 is a side plan view of a lighting assembly within an ecosystem.
Figure 3:
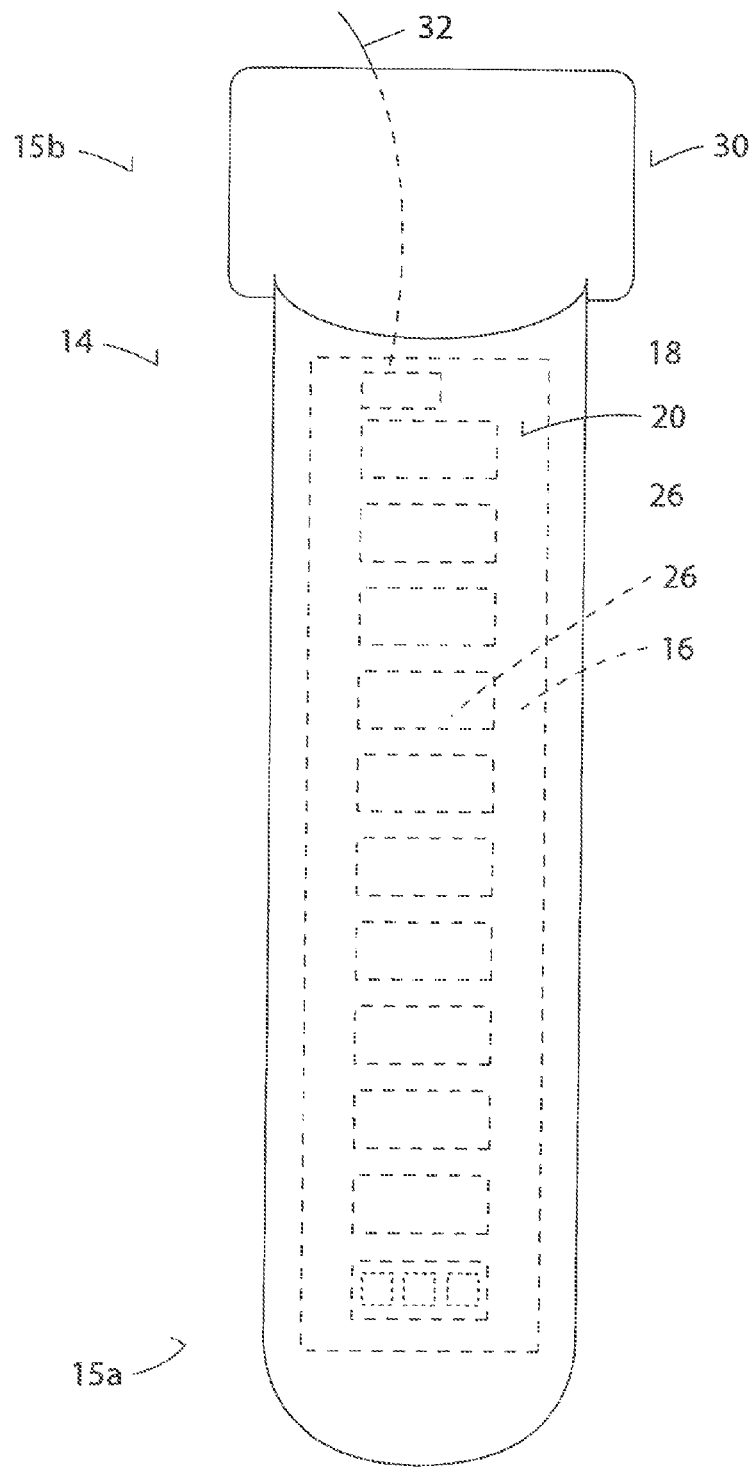
FIG. 3 is a perspective view of a lighting assembly for use in an ecosystem.
Figure 4:
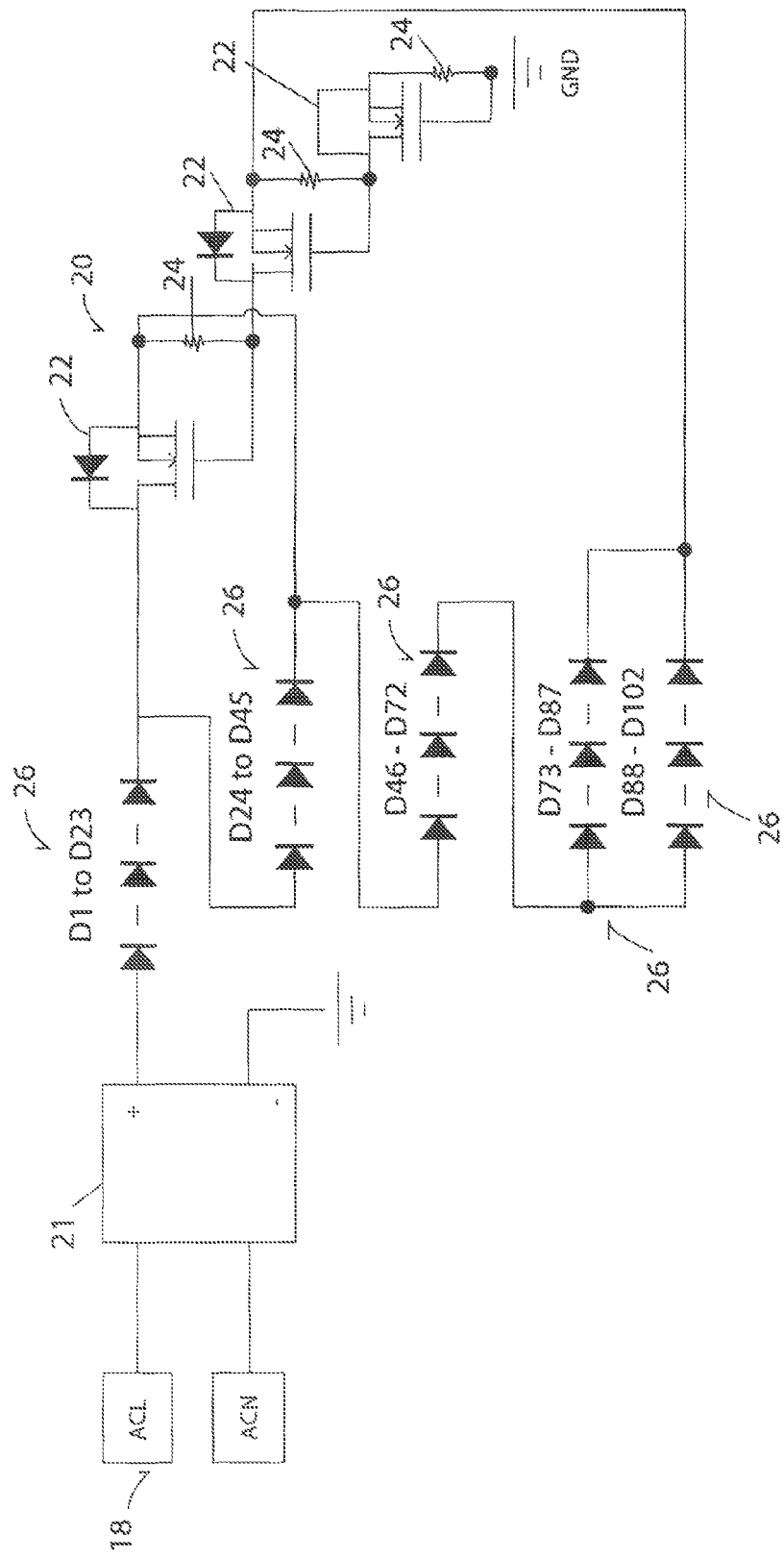
FIG. 4 is a schematic diagram of a lighting assembly for use in an ecosystem.
Figure 5:
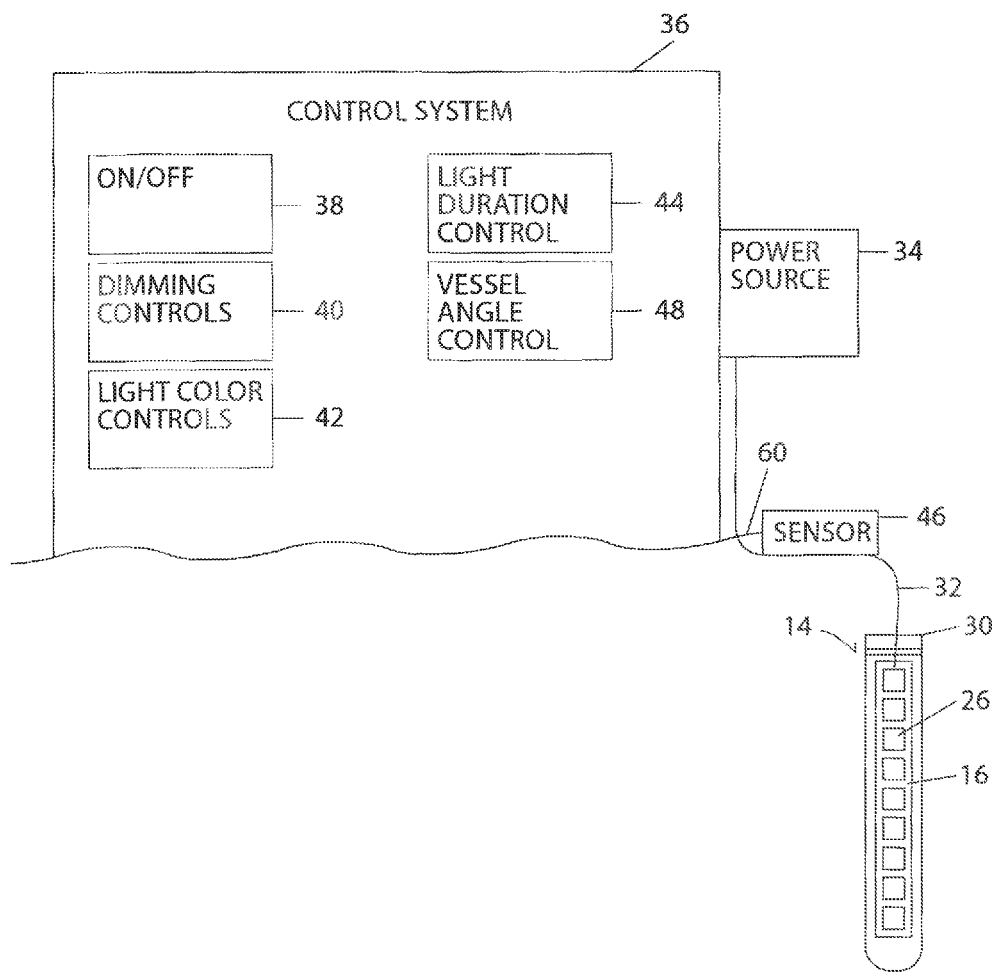
FIG. 5 is a schematic diagram of a lighting assembly with a control assembly for use in an ecosystem.
Figure 6:
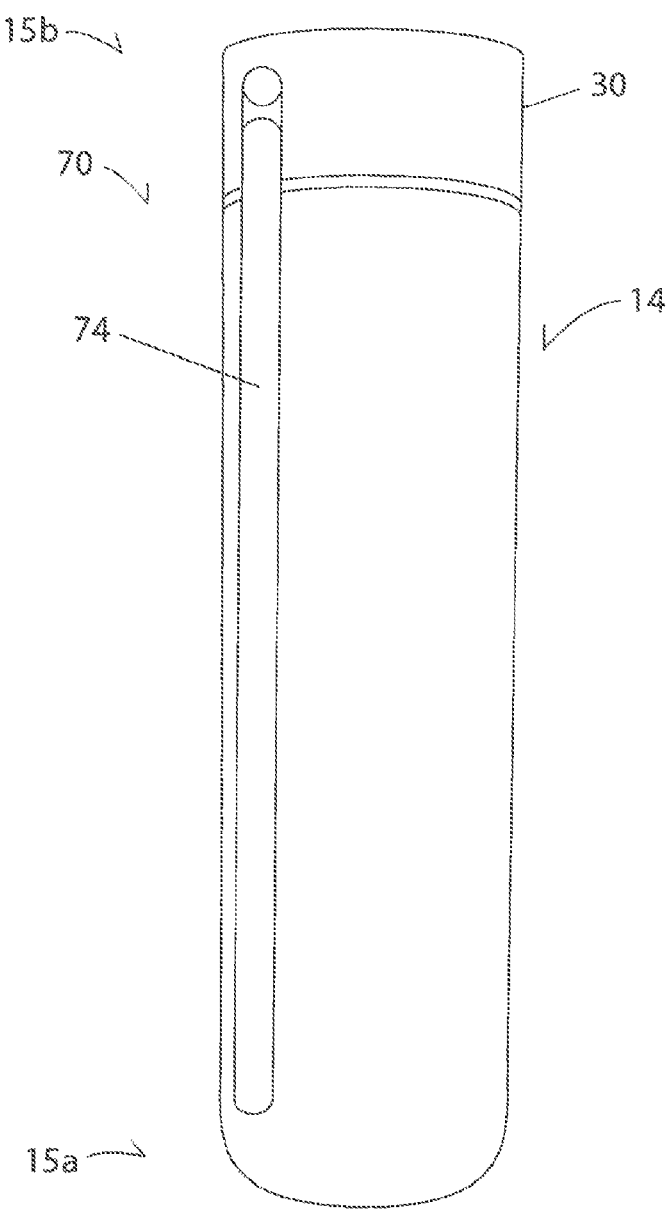
FIG. 6 is a perspective view of a lighting assembly with a cleaning assembly.
Figure 7:
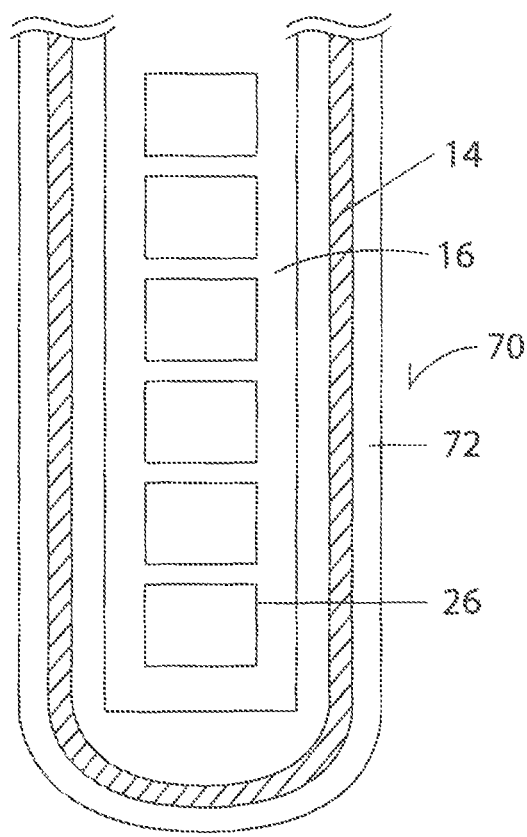
FIG. 7 is a sectional view of a lighting assembly with a cleaning assembly.
Figure 8:
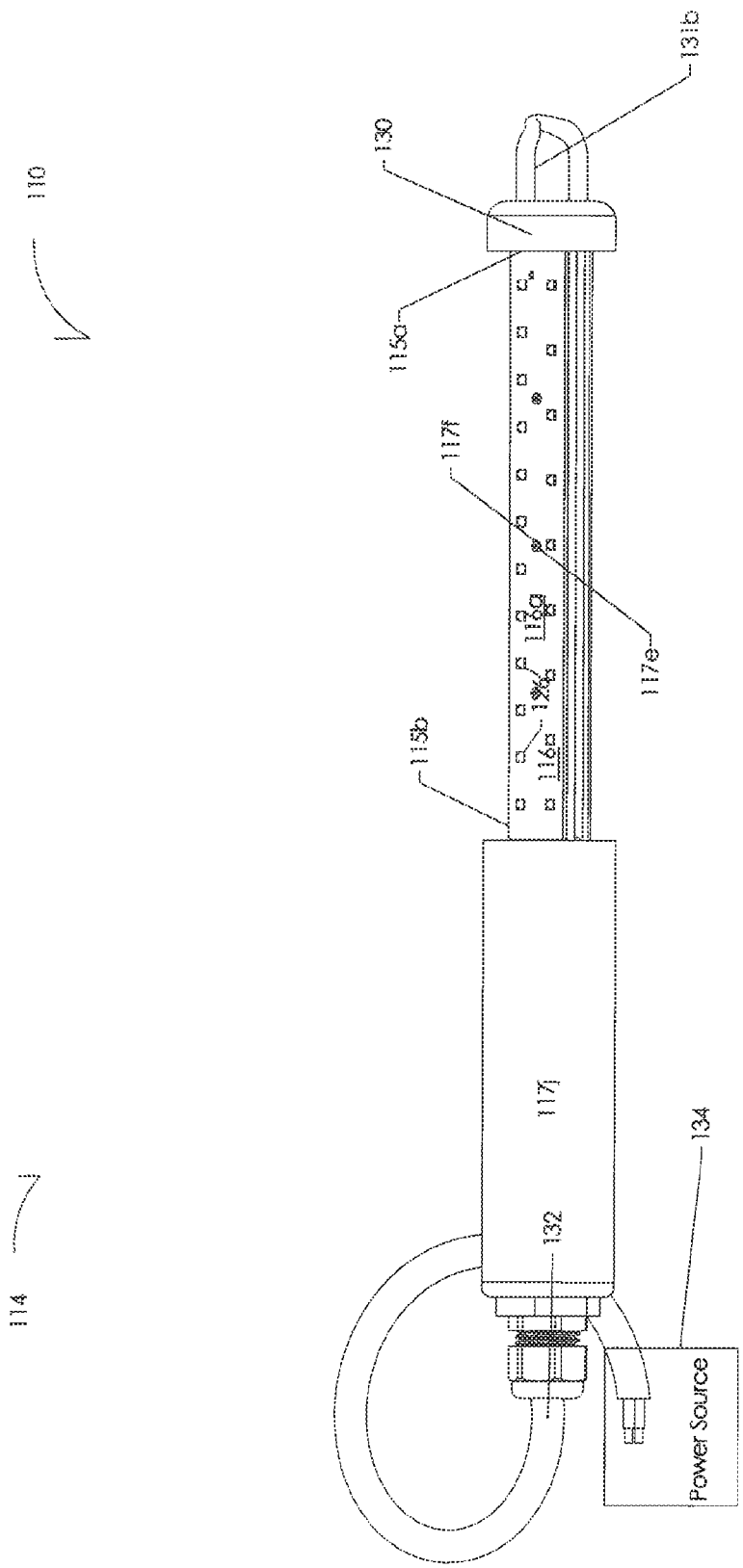
FIG. 8 is a side plan view of a lighting assembly.
Figure 9:
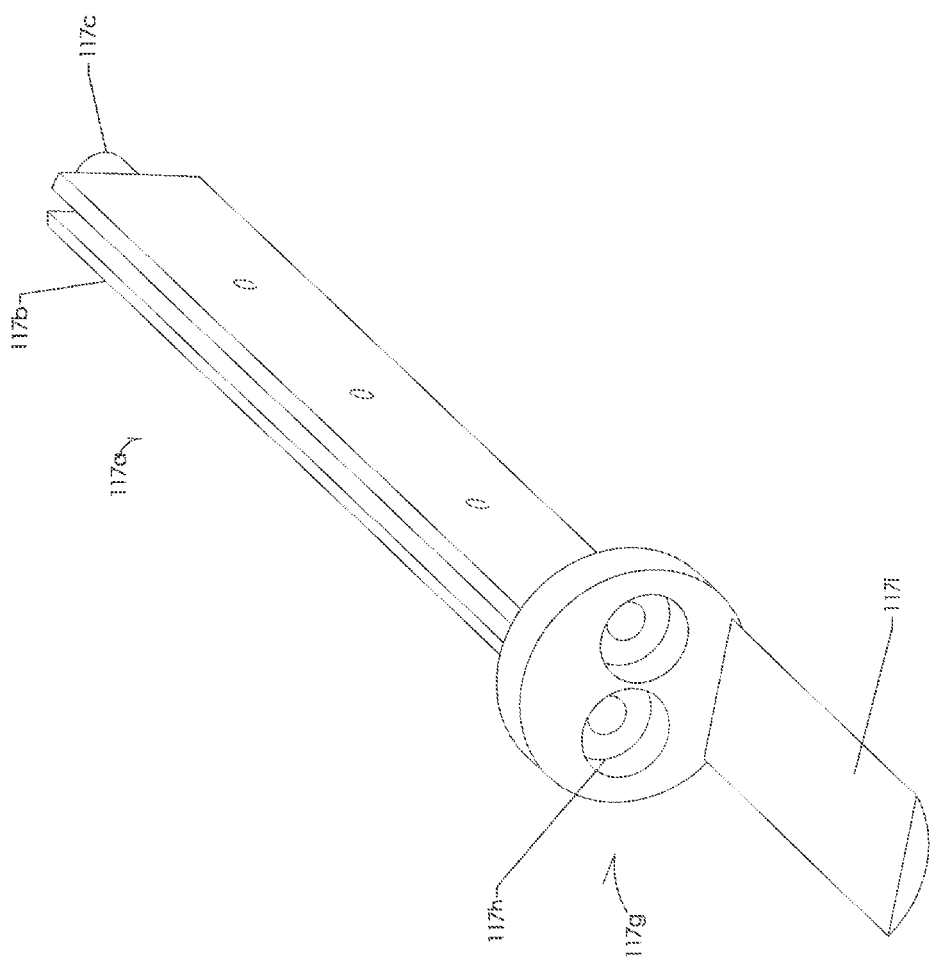
FIG. 9 is a side perspective view of a heat sink for a lighting assembly.
Figure 10:
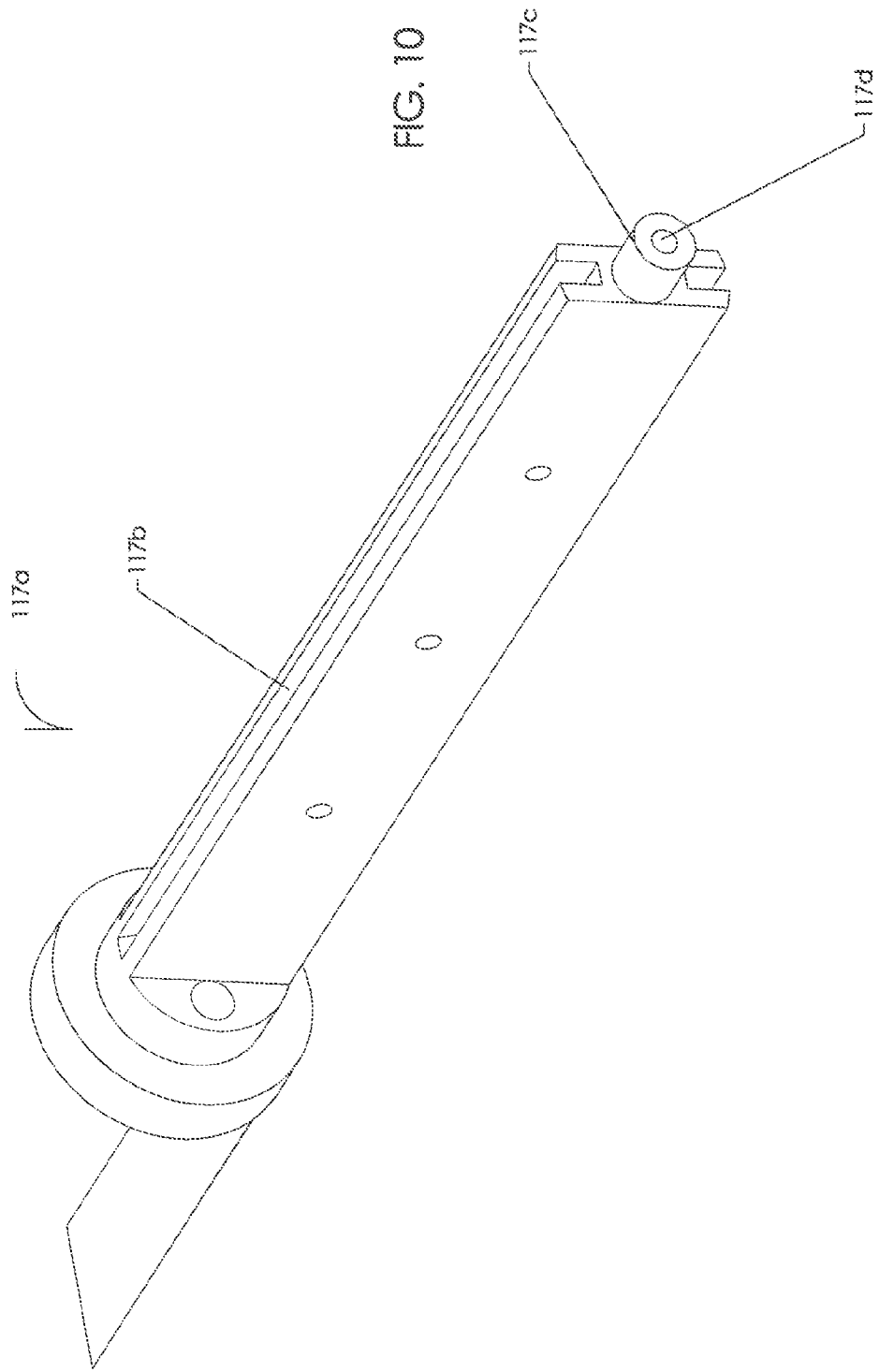
FIG. 10 is a side perspective view of a heat sink for a lighting assembly.
Figure 11:
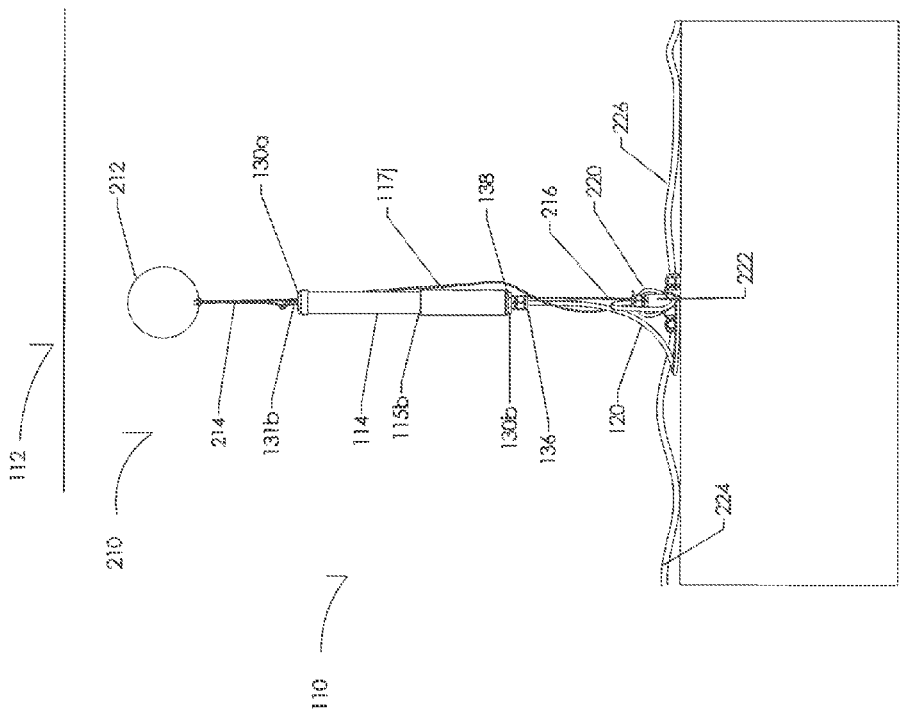
FIG. 11 is a sectional view of a heat sink for a lighting assembly.

The figures show a lighting assembly 10 to be used in an ecosystem 12 that can be either naturally occurring or a natural ecosystem created outdoors in nature, or a man-made ecosystem created indoors. For example, the naturally occurring ecosystem can include a pond, creek, lake, man-made waterway, river, sea, ocean or the like that receives direct lighting from the sun. A man-made ecosystem is one made indoors or within a dwelling, and is either an aquarium, or other indoor aquatic breeding structure that does not directly receive lighting from the sun. Instead, lighting is provided only through windows, interior lighting or the like.

The lighting assembly 10 is a light source capsule that in one embodiment has a capsule or vessel 14 that in one embodiment extends from a closed first end 15a to an opened second end 15b. In a preferred embodiment the vessel 14 is a glass tube. In another embodiment the vessel is square or other shape and made of a clear material to allow the passage of light. The vessel in another embodiment can be made of a material or color, or alternatively have a coating that diffuses light, changes the color of light or materially alters light disposed therethrough.

The vessel 14 surrounds and encloses a substrate 16 that can be of any size or shape. In one embodiment the substrate 16 is rectangular in shape and elongated the length of the vessel. In a preferred embodiment the substrate is a printed circuit board (PCB). Electrically connected to the substrate 16 is a power input 18 that in a preferred embodiment is an AC input and in another embodiment is a DC input. The input current is conditioned by driving circuitry 20 that includes a rectifier 21, at least one transistor 22 and a resistor 24. Protection circuitry such as a fuse or MOV also can be provided as needed. The driving circuitry conditions current for a plurality of light emitting diodes 26. The light emitting diodes 26 can be arranged in series, in series with the driving circuitry 20, in parallel, in parallel with the driving circuitry 20 or in any manner to produce light based on the power input 18 provided, whether AC or DC. In a preferred embodiment the driving circuit 20 and LEDs 26 are arranged as taught in U.S. Patent Pub. No. 2011/0210678 to Grajcar that is incorporated fully herein.

A medium 28 is disposed within the vessel 14 that surrounds the substrate 16. In one embodiment the medium 28 is a fluid and preferably is mineral oil. However, the fluid within the capsule 10 may be selected based on a variety of factors, including specific gravity of the material (e.g., less than the buoyancy created by air in the capsule), heat conductivity, and transparency to light at different wavelengths. The fluid (e.g., oil) within the capsule 14 may thus be selected to maximize heat transfer, to have a specific molecular weight, and/or to have a particular composition.

The medium 28 in one embodiment is clear to allow the passage of light therethrough, though the medium may be altered to be different colors or to have different characteristics to alter the light emitted by the LEDs 26 in order to create different color or wavelengths of light being diffused and emitted from the vessel. The main function of the medium 28 is to transfer heat from the driving circuitry 20 and LEDs 26 to the vessel 14 and thus to the water of the ecosystem 12.

An end cap 30 is removably secured to the opened second end 15b of the vessel 14. Specifically the end cap 30 is of size, shape and design to enclose the opened second end 15b in a sealing manner to prevent seepage of the medium 28 into the water of the ecosystem 12 while preventing water and contaminants carried therein from entering the vessel 14 and damaging the electronics and circuitry 16, 18, 20, 21, 22, 24 and 26. Simultaneously the end cap 30 has electrical wiring 32 disposed therethrough to provide electrical connection between the electronics and circuitry 16, 18, 20, 21, 22, 24 and 26 and an external power source 34. The end cap 30 is designed to provide a sealing connection between the end cap 30 and wiring 32 again to prevent water and contaminants from entering the vessel 14.

A control system 36 is electrically connected to the electrical wiring 32 to provide a user interface to control the operation of the LEDs 26. The control system includes, but is not limited to an on/off switch 38, dimming controls 40, light color controls 42 that in one embodiment is a function of the dimming controls 40 and flicker or light duration control 44 that controls the duration of light emitted by the LEDs 26.

Thus, the lighting assembly 10 optionally has different, independently controllable LEDs 26 so that light having different wavelength spectra can be produced at different positions along the light fixture or light assembly 10 (e.g., different spectra can be produced by lights located at different depths, different spectra can be produced by lights located at different locations, different spectra can be produced depending on a time of day, time of year, or ambient natural light reaching a particular depth in a pond, or the like).

The color of the lights inside the tube or vessel 14 are selected depending on the species of fish or shell fish to be influenced. Different colors affect the growth of different algae or aquatic animals. Adjusting the spectra of lighting can also compensate for differences in latitudes (how much light is reflected, on average, is a function of latitude), incident light on water of an ecosystem 12 such as a pond (e.g., whether the pond is outside under natural light or under a roof), or other factors. For ponds of differing depths, the LEDs 26 may be arrayed from the surface of the pond to the bottom of the pond. At different depths, the light intensity and color may be varied.

For example, outdoor ponds may have lighting designed to supplement or augment the natural lighting incident on the pond. Thus, at the surface of the pond during daylight, less light intensity may be required to be produced by the light fixture, and the light provided may only supplement the spectra filtered by the water. Deeper into the water, more light intensity may be needed and a broader spectra lighting may be needed to provide more broad spectra due to the filtering of the water.

Normally, algae only grow near the surface of the pond because that is where the light that is necessary for growth (photosynthesis) is available. By using additional lighting (including lighting directly within the pond), the lighting assembly 10 can increase the volume of water exposed to light by creating shafts where the light reaches deeper, thus allowing the algae to also grow along the length of the light tube or around the light point source deeper in the water—adding sunlight to more of the water.

The light spectra or intensity may alternatively or additionally be adjusted throughout the circadian day. For example, using independently controllable LEDs 26 arrayed from the surface of the water to the bottom of a pond, or alternatively at a point source (e.g., a single light fixture) within the pond, the intensity and spectra of the light can be adjusted throughout the day. For lighting fixtures or assemblies 10 located closer to the surface, the fixtures may not need to be on during a sunny day (or may have their lighting intensity or spectra adjusted). However, on a cloudy day, in the morning or evening (e.g., at times when greater light is reflected off the surface of the water due to the angle of the sun being low and approaching the critical angle of the water) or at night, the intensity and spectra can be adjusted, for example to increase the brightness and/or spectra adjusted to compensate for different colors of light not penetrating into the water.

For such purposes, a lighting system or assembly 10 may include one or more light sensors 46 electrically connected to the control system 36. In one embodiment the sensors 46 are located at the surface of the water of the ecosystem 12 such as a pond or within the pond, and which are used to measure a natural light intensity and/or spectrum and adjust the lighting intensities and/or spectra of lighting fixtures in the system.

A vessel angling control 48 additionally can be part of the control system 36 that causes mechanical movement of the light assembly 10 to be directed at different angles in the water of an ecosystem 12 or pond. Adjusting for the direction of the light, the light can be adjusted to shine "down" or towards a deeper part of the pond (for example, to stimulate the growth of oysters, clams or scallops), to shine across or towards parts of the pond having similar depths as the light (to influence fish), or to shine up or towards the surface of the pond (for creatures which tend to feed on the surface, like frogs). The directional adjustments may also be performed using a Fresnel or other light directing materials/constructs to direct light in a specific direction.

An anchoring system 50 in one embodiment suspends the lighting assemblies 10 from the surface of the water. Lighting fixtures or assemblies specifically hang from a floating mesh 52. The mesh 52 floats at or near the surface of the pond, and provides a two dimensional matrix from which light fixtures 10 hang into the water. The light fixtures 10 in one embodiment are configured to be heavier than water (or to be weighed), so as to sink in water and into the pond or other ecosystem 12 and be suspended from the floating mesh 52 with a suspension system 54. Multiple light fixtures 10 can be connected along a single cable or suspension member 56 originating from a point on the floating mesh, such that the lighting assemblies 10 provide light at multiple different depths below the origination point.

In another embodiment the lighting assemblies 10 hang from the floating mesh 52 in the water. The suspension member 56 such as cables and/or cords set the depth of the lighting assembly 10. In one embodiment the suspension system 54 includes a cable retraction/retention mechanism 58 and/or a power cord 60. The retraction/retention mechanism 58 (if the power cord 60 is also bearing the weight of the lighting apparatus) floats or holds the excess cable/power cord 60 to allow the length to be adjusted up or down. The wiring 32 that powers the lighting assembly 10 in one embodiment makes up part of the mesh 52 that holds the suspended lighting assemblies 10 in position.

Alternatively, the mesh 52 does not float and instead sinks or is anchored at or near the bottom of the pond, provided a two dimensional matrix from which light fixtures 10 can float up in the water. The light fixtures 10 are configured to be lighter than water, which in one embodiment is accomplished by connecting the vessel 14 to a floating device 62 or floater, so as to float up the vessel 14 in the water and thus anchored by the mesh 52.

Alternatively, the light fixtures 10 are mounted on a stake 64 or other support that sits on the bottom of the pond and holds the light figures at specified distances above the bottom of the pond. Multiple light fixtures 10 are connected along a single cable/stake 64 originating from a point on the mesh 52 (e.g., the light fixtures may be provided at regular 1 meter intervals along the cable/stake 64), such that the light assemblies 10 provide light at multiple different depths above the origination point. In one embodiment the stake 64 is telescoping, which allows the vessel to be positioned at the specific depth of the water of an ecosystem or pool is being maintained and/or allows the lighting to be adjusted as the depth of the pool varies due to any number of reasons, such as environmental reasons.

Alternatively the vessel 14 is simply staked to the bottom of the pond. To avoid puncturing a pond liner, the vessel 14 is on, part of or secured to a standard 66 resting on the bottom of the pond (on the liner, for example). Where standards 66 are used instead of stakes to support the lighting in the water, the standards 66 also play a secondary role of providing habitat to aquatic animals. For example, the standards 66 are optionally designed to provide a variety of underwater structures and overhangs that may be used by aquatic animals seeking shelter.

Alternatively, top lights, if exposed during a drought or low water conditions can be independently controlled (turned off) to reduce energy use. The light assembly 10 rests on a light pole which does not penetrate or damage the liner. The wiring can simply rest along the floor (or may be suspended like wiring between telephone or power poles). A light assembly 10 can adjust the color spectra, or wavelength of the light. The light has different spectra which can be selectively activated to promote growth of different algae, animal species, etc.

Optionally, a cleaning system 70 is provided for the vessel 14. In one embodiment a layer 72 of bio-fouling substance is applied to the surface to the lighting assembly 10 (such as a bio-fouling substance which prevents algae growth on the lighting figure, but does not affect aquatic animals). The bio-fouling substance or treatment may be applied to the surface to the submerged lighting fixture 10 in order to prevent (or retard) the growth and/or attachment of organisms to the fixture. The bio-fouling substance may be a simple silver emitting material, a surfactant, a hydrophobic material, or any other appropriate material or surface treatment. In one example, a material or treatment generally used to prevent algae growth in swimsuits and/or on the bottom of boats is used to reduce growth on submerged items.

Alternatively the cleaning system 70 is a mechanical wiper 74 used to keep the light transmission area (e.g., a window or surface area through which the light is transmitted) clear of growth. The wiper is secured to the vessel 14 and functions to clean the exterior of the vessel as a result of the movement of the wiper 74 along the exterior of the vessel 14.

FIGS. 8-12 show an alternative embodiment of the invention. In this embodiment a lighting assembly 110 is again used in an ecosystem 112 that can be either naturally occurring or a natural ecosystem created outdoors in nature, or a man-made ecosystem created indoors. For example, the naturally occurring ecosystem can include a pond, creek, lake, man-made waterway, river, sea, ocean or the like that receives direct lighting from the sun. A man-made ecosystem is one made indoors or within a dwelling, and is either an aquarium, or other indoor aquatic breeding structure that does not directly receive lighting from the sun. Instead, lighting is provided only through windows, interior lighting or the like.

The lighting assembly 110 is a light source capsule that in one embodiment has a capsule or vessel 114 that in one embodiment extends from an open first end 115a to a second opened second end 115b. In a preferred embodiment the vessel 114 is a glass tube. In another embodiment the vessel is square or other shape and made of a clear material to allow the passage of light. The vessel 114 in another embodiment can be made of a material or color, or alternatively have a coating that diffuses light, changes the color of light or materially alters light disposed therethrough.

The vessel 114 has a vessel wall 114a that surrounds and encloses a substrate 116 that can be of any size or shape. In one embodiment the substrate 116 is rectangular in shape and elongated the length of the vessel 114. In a preferred embodiment the substrate 116 is a printed circuit board (PCB). In the embodiment of FIGS. 8-12 first and second substrates 116a and 116b are secured to and engage an elongated primary heat sink 117a disposed between the first and second substrates 116a and 116b to provide a thermal path from the substrates 116a and 116b to the primary heat sink 117a. The heat sink preferably is made of metal and includes ridges 117b that assist in the conveyance of heat away from the substrates 116a and 116b. While metal is preferred, any material that can be used to convey heat from the substrates 116a and 116b is contemplated by this disclosure. An annular flange 117c extends from the primary heat sink 117a at the second end 115b of the vessel 114 and has an opening 117d disposed therethrough.

In this embodiment fasteners 117e are disposed through openings in the substrates 116a and 116b and engage nut elements 117f to secure the substrates 116a and 116b to the heat sink 117a. While in this embodiment a screw and nut type fastener is provided, other fasteners 117e can be used without falling outside this disclosure.

Extending from the primary heat sink 117a at the end opposite from annular flange 117c is sink element 117g that in one embodiment is generally round and having a diameter that is greater than the diameter of the annular flange 117c. The sink element 117g has openings 117h disposed therethrough. Extending from the sink element is a flange element 117i that in one embodiment provides a surface for receiving a power input 118 and containing driving circuitry 120. The sink element 117g and flange element 117i are of any size and shape and in one embodiment both are rounded and are of size and shape to matingly engage a secondary heat sink 117j that receives and is secured to the vessel 114. In this manner heat is conveyed from the sink element 117g and flange element 117i to the secondary heat sink 117j. In one embodiment the primary heat sink 117a and secondary heat sink 117j are of one piece construction such that they can be made in a single manufacturing step.

In one embodiment the secondary heat sink 117j has interior threads that receive the vessel 114 and epoxy or other water resistant adhesive is used to secure the secondary heat sink 117j to the vessel and provide a watertight seal. In other embodiments that vessel can alternatively be secured to the primary heat sink 117a or secured in other watertight manners without falling outside the scope of this disclosure, including providing a connection point that utilizes a sealing element such as an O-ring or the like.

The secondary heat sink 117j in one embodiment is generally cylindrical having a diameter larger than the diameter of the vessel 114. In this manner the vessel 114 can be received within the secondary heat sink 117j. Preferably the secondary heat sink 117j is made from metal and has a hollow interior such that and openings 117h of sink element 117g to provide a fluid communication path from inside the vessel 114 into the interior of the secondary heat sink 117j.

Electrically connected to each substrate 116a and 116b is the power input 118 that in a preferred embodiment is an AC input and in another embodiment is a DC input. The input current is conditioned by the driving circuitry 120 that provides current for a plurality of light emitting diodes 126. The light emitting diodes 126 can be arranged in series, in series with the driving circuitry 120, in parallel, in parallel with the driving circuitry 120 or in any manner to produce light based on the power input 118 provided, whether AC or DC. In a preferred embodiment the driving circuit 120 and LEDs 126 are arranged as taught in U.S. Patent Pub. No. 2011/0210678 to Grajcar that is incorporated fully herein.

A medium 128 is disposed within the vessel 114 that surrounds the substrates 116a and 116b. In one embodiment the medium 128 is a fluid and preferably is mineral oil. However, the fluid within the capsule 110 may be selected based on a variety of factors, including specific gravity of the material (e.g., less than the buoyancy created by air in the capsule), heat conductivity, and transparency to light at different wavelengths. The fluid (e.g., oil) within the capsule 114 may thus be selected to maximize heat transfer, to have a specific molecular weight, and/or to have a particular composition.

The medium 128 in one embodiment is clear to allow the passage of light therethrough, though the medium may be altered to be different colors or to have different characteristics to alter the light emitted by the LEDs 126 in order to create different color or wavelengths of light being diffused and emitted from the vessel. The main function of the medium 128 is to transfer heat from the driving circuitry 120 and LEDs 126 to the vessel 114 and thus to the water of the ecosystem 112. Further, when the medium 128 is fluid, the fluid flows from the vessel 114 through openings 117h and into the interior of the secondary heat sink 117j. In this manner less expensive, less dense fluid can act as a heat transfer element within the secondary heat sink 117j as opposed to the use of a solid heat sink made only of metal or other heat sinking material.

In one embodiment heat is conveyed to the vessel wall to cause the wall to be at least 60° C. in order to kill any algae or plant life that attempts to grow on the outer vessel wall 114a. In this manner the outer vessel wall 114a does not need to be cleaned and plant life or algae is unable to prevent light from entering the water.

First and second end caps 130a and 130b are removably secured to the second end 115b of the vessel 114 and to an open end of the secondary heat sink 117j. The end caps 130a and 130b are of size, shape and design to enclose the opened end of the vessel 114 and heat sink 117j in a sealing manner to prevent seepage of the medium 128 into the water of the ecosystem 112 while preventing water and contaminants carried therein from entering the vessel 114 and damaging the electronics and circuitry 116, 118, 120, and 126. A sealing element such as an O-ring can also be provided to provide a watertight seal.

A fastening element 131a is disposed through the first end cap 130a and into the opening 117d of annular flange 117c to hold the primary heat sink 117a in place and secure the end cap 130 thereto. Eyelets 131b are spaced apart on either side of the fastening element 131a that have openings disposed therethrough.

Electrical wiring 132 is disposed through the second end cap 130b and through the hollow body of the secondary heat sink 117j to provide an electrical connection between the electronics and circuitry 116, 118, 120 and 126 and an external power source 134. Similarly the electrical wiring 132 can be disposed through the primary heat sink 117a to allow electrical connection points as any desired location to the substrates 116a and 116b.

A nut element 136 and seal 138 are secured around the electrical wiring 132 that is disposed within a cord element 140 and are threadably tightened against the end cap 130b to provide a sealing connection of the wiring 132 through the end cap 130b to prevent the flow of water or liquid into or fluid out of the secondary heat sink 117j.

Figure 12:
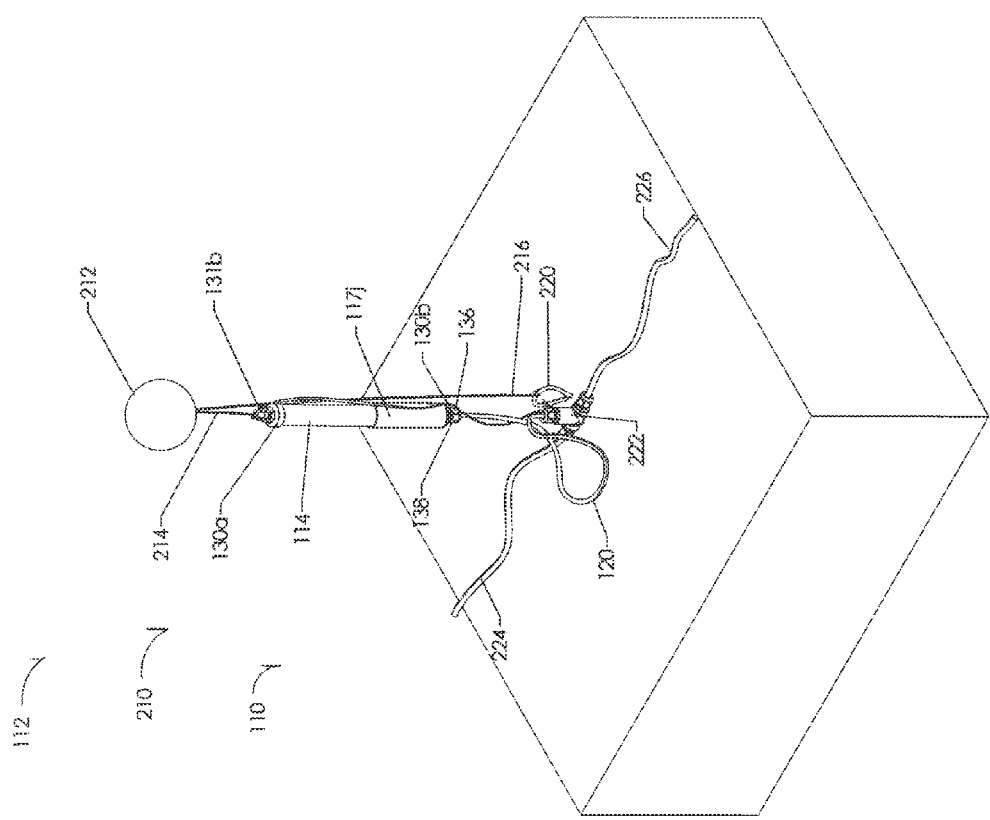
FIG. 12 is a side plan view of a lighting assembly and anchoring system within an ecosystem.

In one embodiment each of the individual lighting assemblies 110 has an anchoring system 210 as provided in FIG. 12. The anchoring system 210 includes a float element 212 that is buoyant in water that can be made of Styrofoam or the like buoyant material. A first connecting element 214 such as a string, twine, wire, teether, strap or the like is fixed to the float element 212. This can be done in any manner as the float element 212 may have an eyelet, or have protrusions around which the connecting element can be wrapped and secured. The connecting element 214 extends from the float element 212 and extends to and is affixed to the lighting assembly 110. In a preferred embodiment the connecting element 214 is secured to the first end cap 130a by disposing the connecting element 214 through the eyelets 131b of the end cap 130a. In this manner the float element 212 prevents the lighting assembly 110 from sinking.

A second connecting element 216 is secured to the float element 212 similar to the first connecting element 214 and is disposed through an eyelet 218 secured to a standard 220 that in a preferred embodiment is a concrete block. The second connecting element 216 is disposed through the eyelet 218 and secured to a wire connector 222 that in a preferred embodiment is a Y connector. Specifically the connector 222 receives the cord element 140 and provides a connection point for first and second electrical lines 224 and 226, the first line 224 extending to a similar wire connector of a second lighting assembly 110 and the second line 226 extending to a third lighting assembly 110 to provide a series connection between the individual lighting assemblies 110. The electrical lines can then be connected to a remote power source for operating the assemblies 110.

In operation the lighting assemblies 10 are placed in water of a predetermined ecosystem 12. The assemblies are positioned in a predetermined position in the water by an anchoring system 50 or 210. In particular, in one embodiment the assemblies are secured to mesh 52 and placed in the water to optimize the growth of aquatic life within the ecosystem 12. The assemblies 10 are then turned on by using the control system 36 that controls the coloring, intensity, light duration and angular position of the assembly 10 to be adjusted based on the predetermined aquatic life within the ecosystem 12 to maximize the growth, yield and physical makeup of the predetermined aquatic life within the ecosystem 12.

Alternatively, in the embodiment with the anchoring system 210 shown in FIG. 12, as a result of the design of the anchoring system 210, the float element 212 provides an upward force on the lighting system 110 with the eyelet 218 providing a point such that the second connecting element 216 provides a downward force on the wire connector 222.

Thus, when sag is provided in the electrical lines 224 and 226 in order to replace the light one need only find the float element 212, detach the first connecting element 214 from the float element 212 and pull up a first lighting assembly 110. As the first lighting assembly 110 is pulled upward the sag in the electrical lines 224 and 226 allows the lighting assembly 110 to be pulled upward, disconnected from the connector 222 and then replaced with a second lighting assembly 110 by connecting the second lighting assembly 110 to the connector 222 and then securing the first connecting element 214 to the lighting assembly 110 similar to the previous lighting assembly 110.

Thus presented is the ability to provide spectra-compensating illumination at a variety of depths in order to encourage and enhance the growth of aquatic animals and/or algae. The color/wavelength spectrum provided may be adjusted based on a variety of factors, including the natural illumination available at the chosen depth, the wavelength spectrum of natural light that is generally found at the chosen depth, the particular needs of the aquatic animals and algae, or the like.

Specifically, spectra-compensating illumination is designed to adapt to animal need. Therefore, the optimum lighting conditions, such as light color/wavelength, intensity and duration is predetermined for each animal and the type of algae that is in a predetermined ecosystem 12. Once the effects on animal behavior and algae is understood, the lighting assembly can either be specifically manufactured to present an assembly having the spectra, intensity and duration needs of the ecosystem or a lighting assembly 10 can be controlled by the control system 36 to provide this output. In this manner the most beneficial of those spectra and conditions is used to further enhance and optimize output of the system used to breed and raise the aquatic animals.

This also includes the concept of accelerating or regulating algae growth. When light is introduced into non-circulating water which has a high nitrogen/$CO_2$ concentration, the light accelerates algae growth, growth that consumes the $CO_2$ and nitrogen. The light may thus be used to reduce the $CO_2$/nitrogen (nitrites) concentration, by encouraging the consumption of the $CO_2$ and nitrogen by algae. As such, lighting assemblies 10 act as an apparatus that is used to lower and/or regulate the $CO_2$ and nitrogen levels in aqua ponds, so as to increase the oxygen levels in the aqua ponds.

The frequencies/wavelengths of sunlight that produce (or permit, cause, enhance, encourage, or favor) photosynthesis can be filtered out by the water and algae found in a pond, such that photosynthesis may not occur deep in the pond. The lighting assemblies 10 may thus be provided that are tunable to produce the frequencies/wavelengths of light required for photosynthesis in water regardless of water depth, sunlight penetration, etc. The lighting assemblies 10 increase the exposure of algae to light by exposing the algae to more photons. The light can be introduced directly into the water to avoid any of the light being reflected from the surface of the water, and thus avoid any reflection of light incident on the water surface at an angle exceeding the critical angle. The light can be used to promote algae growth, and can form part of an apparatus to get the nitrogen and/or $CO_2$ out of the water. The light can alternatively (or additionally) be provided from above the water.

Plants such as algae also require a dark period and individual plants each have an optimum light and dark duration or period. This is discussed further in U.S. Provisional Patent Application No. 61/698,074 that has already been incorporated in full into this application. By using the light duration control 44 of the control system 36 this period may be predetermined and individual assemblies controlled to produce this duration as described in full in the '074 application. Thus algae production is maximized based on predetermining the type of algae presented and its reacts to different lighting parameters and then manufacturing the assembly to meet these parameters or setting an assembly via the control system 36 to meet these parameters.

In addition to applications in aquaculture, the light may be used in other applications to promote algae growth and/or the scavenging or consumption of Nitrogen/$CO_2$. For example, the light may be used in water treatment plants, wastewater treatment applications, pond cleaning applications, or the like.

Also presented is an assembly and method that improves animal growth, which feed on algae, which need light/nitrogen to grow. Therefore, in order to improve animal growth, lighting is used to control the amount of algae available to the animals at different depths and locations.

The lighting assemblies 10 also attract insects to the water surface. The underwater lighting assemblies 10 can also be used to attract insects to the surface of the water, and the insects can then be eliminated by natural biological processes (drowning, decomposition, and or eating). Thus additional food sources are provided.

Further, because of features such as filling the vessel 14 or capsule with a type of medium 28 such as fluid, like mineral oil, multiple LED devices 26 may be placed within a heavy weight glass tube or other vessel 14 and function efficiently. Specifically, the medium oil transfers heat from the LED devices and drivers (or other circuits) to the glass and then to the water. The combination of glass and oil allows the light sources to be cooled into the ambient water, thus enabling the light sources to be run at much higher light outputs (or at higher power levels) than if they were other types of lights or if the tube were filled with air and prevents overheating of the circuitry.

In sum, LEDs 26 located underwater may be used to resolve some or all of the problems discussed. The assemblies 10 can be installed at any economically reasonable depth, such that the growth and presence of beneficial algae at the installed depth becomes possible notwithstanding the presence of light-blocking contamination covering the LEDs or simply the depth of the water. In order to provide maximal algae growth in an ecosystem 12 such as a pond, a lighting system 10 for the pond includes lights arrayed throughout the pond. The lights 10 are distributed throughout the pond, so as to include lights located at different locations within the volume of the pond (e.g., to include lights at different locations of the footprint of the pond and at different pond depths). The orientation and/or grid of light fixtures can be of different sizes and dimensions depending on the depth of the growing pool or pond, the shape of the pool or pond (along a natural coast line, for example), type of water (salinity or opacity), or the size of the growing space. In this manner and as described above the lighting assemblies 10 can be tailored to any ecosystem 12 and type of aquatic life to be grown and either manufactured or actuated to provide an optimized growing based on the use of light. Thus, at the very least, all of the stated objects have been met.

What is claimed:

1. A lighting assembly comprising:
a vessel submerged within water of an ecosystem;
a heat sink at least partially disposed through the vessel;
a first substrate disposed within the vessel and having driving circuitry thereon;
at least one lighting device electrically connected to the driving circuitry that emits light within the water of the ecosystem; and
wherein heat from the circuitry is conveyed through the heat sink to the water;
wherein the heat sink comprises a primary heat sink disposed within the vessel that is engaged by the substrate to provide a thermal path from the substrate to the primary heat sink; and
wherein the heat sink further comprises a secondary heat sink extending from the primary heat sink away from the vessel.

2. The lighting assembly of claim 1 wherein the diameter of the secondary heat sink is greater than the diameter of the vessel.

3. The lighting assembly of claim 2 wherein the vessel is sealingly connected within the secondary heat sink.

4. The lighting assembly of claim 1 wherein the primary heat sink and secondary heat sink are of one piece construction.

5. The lighting assembly of claim 1 wherein the primary heat sink has ridges to convey heat from the first substrate.

6. The lighting assembly of claim 1 wherein the secondary heat sink has a hollow interior that receives wiring that is electrically connected to the driving circuitry.

7. The lighting assembly of claim 1, wherein a medium is within the vessel surrounding the substrate to convey heat to a vessel wall.

* * * * *